United States Patent [19]

Woodbury et al.

[11] Patent Number: 5,710,295
[45] Date of Patent: Jan. 20, 1998

[54] PREPARATION OF ALKALI METAL ACYL AMINO ACIDS

[75] Inventors: Richard P. Woodbury, Amherst; Roger R. Gaudette, Litchfield; F. David Wood, Epsom, all of N.H.

[73] Assignee: Hampshire Chemical Corp., Lexington., Mass.

[21] Appl. No.: 466,094

[22] Filed: Jun. 6, 1995

[51] Int. Cl.$^6$ .................................. C07C 231/00
[52] U.S. Cl. ................. 554/69; 554/68; 554/133; 554/138
[58] Field of Search ............... 554/68, 69; 564/133, 564/138

[56] References Cited

U.S. PATENT DOCUMENTS

| | | | |
|---|---|---|---|
| 2,962,448 | 11/1960 | Dvorkovitz, et al. | 252/152 |
| 3,836,551 | 9/1974 | Schroeder et al. | 260/404 |
| 4,380,646 | 4/1983 | Franzmann | 548/502 |

FOREIGN PATENT DOCUMENTS

| | | |
|---|---|---|
| 9507881 | 3/1995 | WIPO . |
| 95/33033 | 12/1995 | WIPO . |

*Primary Examiner*—Gary Geist
*Assistant Examiner*—Deborah D. Carr
*Attorney, Agent, or Firm*—Neilds, Lemack & Dingman

[57] ABSTRACT

A process of preparing alkali metal N-acyl amino acids, especially sodium N-acyl sarcosinates. The process of the invention eliminates the use of phosphorus trichloride or thionyl chloride and carboxylic acid chlorides. The process involves reacting the alkali metal N-acyl amino acid directly with a fatty acid at elevated temperatures with constant removal of water generated in the reaction.

9 Claims, No Drawings

PREPARATION OF ALKALI METAL ACYL AMINO ACIDS

BACKGROUND OF THE INVENTION

The use of sarcosinate surfactants, and in particular, N-acyl sarcosinates, in the manufacture of soap is well known. Typically the sarcosinate is used in the form of its sodium, potassium or ammonium salt solution. N-acyl sarcosinates are produced commercially by the Schotten-Baumann reaction of the sodium salt of sarcosine with the appropriate fatty acid chloride under carefully controlled conditions:

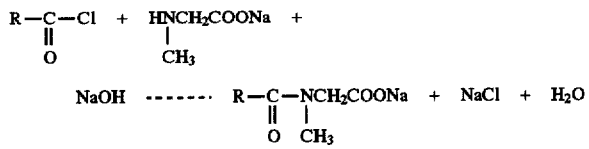

After the reaction is complete, the crude sodium salt is acidified to liberate the N-acyl sarcosine acid which is separated from the aqueous by-products. It then is neutralized to a salt form. Sarcosinates such as sodium lauroyl sarcosinate, sodium cocoyl sarcosinate and sodium myristoyl sarcosinate are commercially available under the trademark HAMPOSYL® from Hampshire Chemical Corp.

N-Acyl sarcosinates also have been used for many years in areas such as oral, skin and hair care. They have been shown to reduce the permeation of potentially irritating solutes, such as sodium ions, through human skin; whereas other surfactants were shown to increase the permeation ("The Influence of Detergents and Surfactants on Epidermal Permeability", Bettley, F. Ray, *Brit. J. Dermatol.*, 77, 98–100 (1965)). N-Acyl sarcosinates have also been shown to reduce the skin irritation normally associated with detergent formulations when incorporated as co-surfactants (U.S. Pat. No. 2,962,448). N-Acyl sarcosinates exhibit low toxicity to mammals and fish, have a low tendency to cause irritation, and biodegrade extremely rapidly.

It would therefore be desirable to simplify the process for manufacturing N-acyl sarcosinates, as well as other N-acyl amino acids, and to eliminate environmental drawbacks of the conventional processes.

SUMMARY OF THE INVENTION

The problems of the prior art have been solved by the instant invention, which provides a process of preparing alkali metal N-acyl amino acids, especially sodium N-acyl sarcosinates. The process of the invention eliminates the use of phosphorus trichloride or thionyl chloride and carboxylic acid chlorides. In general terms, the instant process involves reacting the alkali metal N-acyl amino acid directly with a fatty acid at elevated temperatures with constant removal of water generated in the reaction.

DETAILED DESCRIPTION OF THE INVENTION

The starting reactants for the process of the present invention are a fatty acid having the generic formula RCOOH, and an amino acid in which the amino group is substituted by at least one hydrogen atom. Reacting the fatty acid and amino acid at elevated temperatures results in the formation of acyl amino acid, but significant color and by-product formation is evident. It is therefore surprising that color and by-product formation is minimal under the reaction conditions utilized in the present invention.

Suitable fatty acids include straight chain aliphatic, branched chain aliphatic, cycloaliphatic, saturated and unsaturated, aromatic and heteroaromatic carboxylic acids, such as acetic, propionic, butyric, caprylic, caproic, nonanoic, 3,5,5-trimethylhexanoic, nonanoic, decanoic, undecanoic, lauric, myristic, palmitic, stearic, oleic, linoleic, behenic, 2-methyl-undecanoic, 2-butyl-octanoic, 2-ethyl-hexanoic, alkylsuccinic, alkenylsuccinic, adipic, cyclohexyl, benzoic, chloro-benzoic, nitrobenzoic, naphthenic, abietic, nicotinic, 2-pyridine-carboxylic, terephthalic, phthalic, $C_8(EO)_2COOH$, and mixtures thereof. Preferred fatty acids include $C_8$–$C_{20}$ carboxylic acids, preferably oleic acid ($CH_3(CH_2)_7CH:CH(CH_2)_7$—COOH), lauric acid ($CH_3(CH_2)_{10}COOH$), myristic acid ($CH_3(CH_2)_{12}COOH$), and coconut acid, to prepare oleoyl sarcosine, lauroyl sarcosine, myristoyl sarcosine and cocoyl sarcosine, respectively.

Suitable amino acids are those wherein the amino group has at least one substitutable hydrogen atom. Preferred amino acids include the alkali metal salts of sarcosine, glycine, iminodiacetic acid, alanine, N-methylalanine, β-alanine, N-methyl-β-alanine, aspartic acid, N-methyl aspartic acid, valine, leucine, isoleucine, cystine, methionine, phenylalanine, glutamic acid, proline and lysine. Sodium sarcosinate is especially preferred.

Using a 1:1 ratio of the fatty acid to alkali metal amino acid results in a 50–55% product yield, regardless of the reaction time. Moreover, excess alkali metal amino acid does not assist in pushing the reaction to completion. Accordingly, it is preferred that excess amino acid be added to the reaction mixture of alkali metal amino acid and fatty acid to speed up the reaction and achieve higher conversions. The inventors of the present invention have found that the addition of one equivalent of excess amino acid based on fatty acid results in an 85–90% conversion in 8–10 hours. The addition of two equivalents results in 90% conversion in 3–5 hours. More or less amino acid can be used depending upon the desired conversion and rate. The acid can be added incrementally or all at once.

Operable reaction temperatures are from about 100° to about 200° C. At temperatures below about 170° C. the reaction tends to be too slow. Accordingly, a temperature of 170° C.–190° C. is preferred, with 170° C. being especially preferred.

Preferably the alkali metal amino acid starting material is used in dry form. The crude reaction mixture is worked up by diluting it in a solution of isopropanol in water, preferably in a ratio of isopropanol:water of from 95:5 to 5:5. It is preferred that the amount of isopropanol be minimized. The crude solution is then acidified to a pH of 1 which causes a phase split. Suitable acids for acidification include mineral acids and sulfuric acid, with sulfuric acid being preferred. The organic lighter portion is separated and the isopropanol and water are removed by evaporation.

Alternatively, the starting material can be the amino acid, which could be neutralized with aqueous base such as sodium hydroxide and then spray dried to produce dry sodium salt of the amino acid.

In order to avoid the formation of color bodies, it is important that oxidation be minimized or eliminated. This can be accomplished with an inert gas (such as nitrogen) purge, or by aplying vacuum. This can also serve to remove the water that is formed during the condensation of the fatty acid with the alkali metal amino acid.

The invention is further illustrated by the following examples, which are provided for purpose of illustration and are not to be construed as limiting.

EXAMPLE 1

11.04 grams (0.124 mole) of sarcosine acid was added to 104 grams of methanol, followed by the addition of 26.8 grams (0.124 mole) of 25% sodium methoxide. The resulting mixture was refluxed for 15 minutes at which time the solution became homogeneous. The oleic acid was added in one portion and the methanol was removed by distillation. After complete removal of the methanol, the temperature of the reaction mixture was increased to 170° C. At 4.0, 5.5 and 6.5 hours, an additional 2.8 g (0.031 mole) of sarcosine acid was added and heating continued at 170° C. The reaction was heated for a total of 8.5 hours and the final ratio of sodium oleoyl safcosine to oleic acid was 85:15 (determined by HPLC area count).

EXAMPLE 2

A reactor equipped with a mechanical stirrer, heating mantle, thermometer, and a nitrogen atmosphere, was charged with 35.04 g (0.125 mole) of oleic acid. The oleic acid was heated to 80° C. and 13.8 g (0.125 mole) of solid sodium sarcosinate was added. This mixture was heated to 170° C. with a constant nitrogen sparge. When the reaction mixture reached 170° C., 11.4 g (0.125 mole) of solid sarcosine acid was added. The reaction mixture was sampled after ten hours at 170° C. and the conversion based on oleic acid was 84.2%.

The crude reaction mixture was dissolved in 60 g of a 50:50 volume ratio of isopropanol and water. This solution was acidified with sulfuric acid to a pH of 1. Upon acidification, the solution formed two layers. The upper layer, containing the product, was separated and concentrated resulting in N-oleoyl sarcosine.

EXAMPLE 3

A reactor equipped with a mechanical stirrer, heating mantle, thermometer, and a nitrogen atmosphere, was charged with 35.04 g (0.125 mole) of oleic acid. The oleic acid was heated to 80° C. and 13.8 g (0.125 mole) of solid sodium sarcosinate was added. This mixture was heated to 170° C. with a constant nitrogen sparge. When the reaction mixture reached 170° C., 22.8 g (0.250 mole) of solid sarcosine acid was added. The reaction mixture was sampled after five hours and the conversion based on oleic acid was 92.5%.

EXAMPLE 4

A three neck, 500 ml. round bottom flask equipped with mechanical stirring, a thermometer, a nitrogen inlet, and a nitrogen outlet was charged with 35.70 g (0.175 mole) of lauric acid. Under a constant nitrogen sparge the lauric acid was heated to 160° C. and 19.40 g of a sodium sarcosinate and 15.90 g of sarcosine acid (0.175 mole) were added as rapidly as possible. The mixture was then heated to 170° C. under a constant nitrogen sparge to remove the water formed during the reaction. Samples were removed periodically to monitor the disappearance of lauric acid. After seven hours, 93% of the lauric acid was converted to products.

EXAMPLE 5

A three neck, 500 ml round bottom flask equipped with mechanical stirring, a thermometer, a nitrogen inlet, and a nitrogen outlet was charged with 49.00 g (0.175 mole) of oleic acid. Under a constant nitrogen sparge the oleic acid was heated to 160° C. and 8.60 g (0.088 mole) of a sodium glycinate and 6.60 g of glycine acid (0.088 mole) were added as rapidly as possible. The mixture was then heated to 170° C. under a constant nitrogen sparge to remove the water formed during the reaction. Samples were removed periodically to monitor the disappearance of oleic acid. After 3.5 hours, 45.8% of the oleic acid was converted to products.

EXAMPLE 6

A three neck, 500 ml round bottom flask equipped with mechanical stirring, a thermometer, a nitrogen inlet and a nitrogen outlet was charged with 34.76 g (0.124 mole) of oleic acid. Under a constant nitrogen sparge, the oleic acid was heated to 160° C. and 13.78 g (0.124 mole) of a sodium sarcosinate was added as rapidly as possible. The mixture was then heated to 170° C. under a constant nitrogen sparge to remove the water formed during the reaction. Samples were removed periodically and the progress of the reaction was monitored by HPLC. After six hours, 55% of the oleic acid was converted to products. The reaction was heated at 170° C. for an additional four hours (ten total hours) and the conversion was 57%.

EXAMPLE 7

A three neck, 500 ml round bottom flask equipped with mechanical stirring, a thermometer, a nitrogen inlet and a nitrogen outlet was charged with 42.05 g (0.150 mole) of oleic acid. Under a constant nitrogen sparge, the oleic acid was heated to 160° C. and 20.50 g (0.23 mole) of a sarcosine acid was added as rapidly as possible. The mixture was then heated to 160° C. under a constant nitrogen sparge to remove the water formed during the reaction. Samples were removed periodically and the progress of the reaction was monitored by HPLC. After five hours, 75% of the oleic acid was converted to products.

What is claimed is:

1. A process for producing alkali metal N-acyl amino acid, comprising reacting a fatty acid having the formula RCOOH wherein R is a $C_1$ or higher hydrocarbyl substituent with (a) an alkali metal amino acid in which the amino group is substituted with at least one hydrogen atom, and (b) the acid of said alkali metal amino acid.

2. The process of claim 1, wherein said fatty acid is selected from the group consisting of oleic acid, lauric acid, myristic acid, coconut acid, stearic acid, nonanoic acid, decanoic acid and undecanoic acid.

3. The process of claim 1, wherein said fatty acid is lauric acid.

4. The process of claim 1, further comprising continuously removing water from the reaction medium as it is formed.

5. The process of claim 4, wherein said water is removed by sparging with an inert gas.

6. The process of claim 1, wherein the reaction is carried out at a temperature of from 170° C. to 190° C.

7. The process of claim 1, wherein said acid of said alkali metal amino acid is added in an amount of one equivalent excess based upon said fatty acid.

8. The process of claim 1, wherein said acid of said alkali metal amino acid is added in an amount of two equivalents excess based upon said fatty acid.

9. The process of claim 1, wherein said alkali metal amino acid is selected from the group consisting of alkali metal sarcosine, alkali metal glycine, alkali metal iminodiacetic acid, alkali metal alanine, alkali metal N-methylalanine, alkali metal β-alanine, alkali metal N-methyl-β-alanine, alkali metal aspartic acid, alkali metal N-methyl aspartic acid, alkali metal valine, alkali metal leucine, alkali metal isoleucine, alkali metal cystine, alkali metal methionine, alkali metal phenylalanine, alkali metal glutamic acid, alkali metal proline, and alkali metal lysine.

* * * * *